United States Patent [19]
Appleton et al.

[11] 4,296,114
[45] Oct. 20, 1981

[54] 3,4-DIHYDRO-3-OXOPYRIDO[2,3-B]-PYRAZINES, COMPOSITIONS AND USE THEREOF

[75] Inventors: Richard A. Appleton; David Johnston, both of Loughborough, England

[73] Assignee: Fisons Limited, London, England

[21] Appl. No.: 63,357

[22] Filed: Aug. 2, 1979

[30] Foreign Application Priority Data

Aug. 15, 1978 [GB] United Kingdom ............... 33431/78
Dec. 13, 1978 [GB] United Kingdom ............... 48438/78

[51] Int. Cl.³ ................ A61K 31/495; A61K 31/535; C07D 471/08
[52] U.S. Cl. ........................ 424/248.52; 424/248.54; 424/250; 544/80; 544/117; 544/350
[58] Field of Search .................. 544/80, 117, 350; 424/248.5, 248.53, 248.56, 248.57, 248.58, 250, 248.52

[56] References Cited

U.S. PATENT DOCUMENTS

4,091,219  5/1978  Denzel et al. ..................... 544/350

*Primary Examiner*—Henry R. Jiles
*Assistant Examiner*—R. W. Ramsuer
*Attorney, Agent, or Firm*—Merriam, Marshall & Bicknell

[57] ABSTRACT

There are described compounds of formula I,

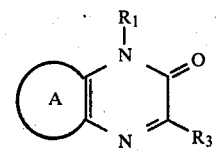

in which $R_1$ is phenyl substituted by halogen, alkoxy, alkyl, carboxy-alkyl, —$NR_4R_5$, carboxy or alkoxy carbonyl, $R_3$ is hydrogen, alkyl, mono- or di-carboxy alkyl, halo, alkoxy, phenyl, halo-phenyl, hydroxy, phenoxy, thiol, thioalkoxy, thiophenoxy, —$NR_4R_5$, cyano, —COOH, carboxyureido, —$CF_3$, —$COR_6$, hydroxyalkyl, aminoalkyl, or alkoxy substituted by $NR_4R_5$, ring A is a benzene or a pyridine ring which optionally carries up to 4 substituents $R_3$, which may be the same or different, $R_4$ and $R_5$, which may be the same or different, each represent hydrogen, phenyl, halophenyl or alkyl, the alkyl optionally being substituted by alkoxy or by a mono- or di-alkyl or unsubstituted amino group; or $R_4$ and $R_5$, together with the nitrogen atom to which they are attached, form a piperidine, morpholine or an optionally alkyl substituted piperazine ring, and $R_6$ is hydrogen or alkyl, provided that (i) when $R_1$ is phenyl substituted by chlorine or bromine, ring A is not a benzene ring substituted by chlorine or bromine, or (ii) when $R_1$ is phenyl substituted by methoxy $R_3$ is not phenyl, and pharmaceutically acceptable salts, esters and amides thereof.

There are also described methods for making the compounds and pharmaceutical, e.g. anti-inflammatory, compositions containing the compounds.

10 Claims, No Drawings

3,4-DIHYDRO-3-OXOPYRIDO[2,3-B]-PYRAZINES, COMPOSITIONS AND USE THEREOF

This invention relates to new compounds, methods for their preparation and compositions containing them.

According to the invention we provide compounds of formula I,

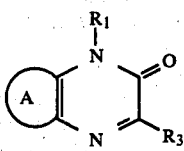

in which $R_1$ is phenyl substituted by halogen, alkoxy, alkyl, carboxy-alkyl, $-NR_4R_5$, carboxy or alkoxy carbonyl, $R_3$ is hydrogen, alkyl, mono- or di-carboxy alkyl, halo, alkoxy, phenyl, halo-phenyl, hydroxy, phenoxy, thiol, thioalkoxy, thiophenoxy, $-NR_4R_5$, cyano, $-COOH$, carboxyureido, $-CF_3$, $-COR_6$, hydroxyalkyl, aminoalkyl, or alkoxy substituted by $NR_4R_5$, ring A is a benzene or pyridine ring which optionally carries up to 4 substituents $R_3$, which may be the same or different, $R_4$ and $R_5$, which may be the same or different, each represent hydrogen, phenyl, halophenyl or alkyl, the alkyl optionally being substituted by alkoxy or by a mono- or di-alkyl or unsubstituted amino group; or $R_4$ and $R_5$, together with the nitrogen atom to which they are attached, form a piperidine, morpholine or an optionally alkyl substituted piperazine ring, and $R_6$ is hydrogen or alkyl, provided that (i) when $R_1$ is phenyl substituted by chlorine or bromine, ring A is not a benzene ring substituted by chlorine or bromine, or (ii) when $R_1$ is phenyl substituted by methoxy $R_3$ is not phenyl, and pharmaceutically acceptable salts, esters and amides thereof.

According to the invention we also provide a process for the production of a compound of formula I, or a pharmaceutically acceptable salt, ester or amide thereof, which comprises (a) producing a compound of formula I in which $R_3$ is other than alkoxy, halo or alkoxy substituted by $NR_4R_5$, by reacting a corresponding compound of formula II,

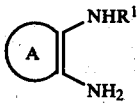

or a salt thereof, in which $R_1$, A and the provisos are as defined above, with a compound of formula III, $$R_8CO-COOR_7 \quad \text{III}$$

in which $R_8$ has the same significances as $R_3$ above, save that $R_8$ is other than alkoxy, halo, or alkoxy substituted by $NR_4R_5$, or a precursor thereof, and $R_7$ is hydrogen or alkyl, or, when $R_3$ in the compound of formula I is to be a carboxy ureido group, reacting the compound of formula II with alloxan, (b) producing a compound of formula I in which $R_3$ is halogen, by reacting a corresponding compound of formula I in which $R_3$ is $-OH$ with an appropriate halogenating agent, (c) producing a compound of formula I in which $R_3$ is $-NR_4R_5$, alkoxy, alkoxy substituted by $-NR_4R_5$, phenoxy, thiol, thioalkoxy, thiophenoxy or cyano, by reacting a corresponding compound of formula I in which $R_3$ is halogen, with a compound $HNR_4R_5$, an unsubstituted or an $-NR_4R_5$ substituted alkoxide, a phenoxide, a sulphide, a thioalkoxide, a thiophenoxide or a cyanide, (d) producing a compound of formula I in which $R_3$ is hydroxy methyl by selective reduction of a corresponding compound of formula I in which $R_3$ is $-COOH$, (e) producing a compound of formula I in which $R_3$ is an unsubstituted amide group by selective hydrolysis of a corresponding compound of formula I in which $R_3$ is $-CN$ (f) producing a compound of formula I in which $R_3$ is $-NH_2$ by reacting a corresponding compound of formula I in which $R_3$ is alkoxy with ammonia, (g) selective dehydrogenation of a compound of formula IV,

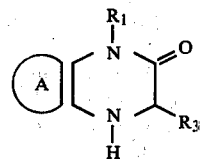

in which $R_1$, $R_3$, A and the proviso are as defined above, (h) producing a pharmaceutically acceptable acid addition salt of a basic compound of formula I by reacting a basic compound of formula I with an appropriate acid, and if desired or necessary converting a basic or acidic compound of formula I to a pharmaceutically acceptable salt, ester or amide thereof, or vice versa.

The reaction of process (a) is preferably carried out at an elevated temperature, e.g. at a temperature of from about 20° to 200° C. The reaction may be carried out in an excess of the compound of formula III as solvent and/or in the presence of another solvent which is inert under the reaction conditions, e.g. ethanol. When a dialkyl oxalate is used as the compound of formula III the product is a compound of formula I in which $R_3$ is $-OH$.

Process (b) may be carried out using a suitable halogenating agent, e.g. phosphorus oxychloride, phosphorus pentachloride or $SOCl_2$. We prefer to use an excess of the halogenating agent and to carry out the reaction under anhydrous conditions. The reaction is preferably carried out at a temperature of from 20° to 150° C.

Process (c) may be carried out using an excess of the amine (or of the other compound used to react with the compound of formula I in which $R_3$ is halogen) as the solvent or using a solvent which is inert under the reaction conditions, e.g. a lower alkanol, toluene, tetrahydrofuran or dimethylformamide. The reaction may, if desired, be carried out in the presence of an acid acceptor. The reaction may be carried out at a temperature of from about 20° to 100° C. We prefer to use a metal, e.g. an alkali metal, alkoxide, phenoxide, sulphide, thioalkoxide, thiophenoxide, or cyanide.

Process (d) may be carried out using a reducing agent such as BH$_3$.(CH$_3$)$_2$S complex. The reduction may conveniently be carried out in a solvent which is inert under the reaction conditions, e.g. tetrahydrofuran, and at a temperature of from about 20° to 60° C.

The hydrolysis of process (e) may be carried out under acidic conditions, e.g. in the presence of polyphosphoric acid. The hydrolysis is preferably carried out at an elevated temperature, e.g. of from 50° to 150° C.

The reaction of process (f) may be carried out at an elevated temperature, e.g. of from about 150° to 250° C. The ammonia may conveniently be generated in situ by use of an ammonium salt, e.g. ammonium acetate.

The dehydrogenation of process (g) may be effected by oxidation, e.g. using a mild oxidising agent such as manganese dioxide. The reaction may be carried out in a solvent which is inert under the reaction conditions, e.g. a chlorinated hydrocarbon such as dichloromethane. The reaction may be carried out at a temperature of from about 0° to 50° C. We prefer R$_3$ not to be a halogen atom.

Process (h) may be carried out using conventional salt etc forming techniques.

Compounds of formulae II, III and IV are either known or may be made from known compounds by methods known per se.

Compounds of formula IV may be made for example by reduction, e.g. with zinc and glacial acetic acid, of a corresponding compound of formula I.

The compounds of formula I and intermediates therefore may be isolated and purified using techniques known per se, e.g. crystallisation. The compounds of formula I may, where appropriate, be purifed by conversion to a suitable salt, recrystallisation of the salt, and regeneration of the free base by treatment of the salt with a suitable base.

Pharmaceutically acceptable salts of basic compounds of formula I include acid addition salts with organic acids, e.g. acetic, citric, tartaric or maleic acid; or preferably salts with inorganic acids, e.g. hydrochloric, sulphuric or nitric acid. When one of the substituents R$_1$ and R$_3$ contain a —COOH group basic addition salts, esters, e.g. C 1 to 6 alkyl esters, and amides, e.g. unsubstituted or mono- or di- C 1 to 6 alkyl amides, may be formed and are included in the invention.

The compounds of formula I, and pharmaceutically acceptable salts, esters and amides thereof, are useful because they possess pharmacological activity in animals. In particular the compounds are useful as anti-inflammatory agents as indicated by the developing adjuvant-induced polyarthritis test in rats Pearson C. M. (1956) Proc, Soc. exp. Biol. N.Y., 91, 95 or in the guinea pig pleurisy test set out in Example A. The compounds are therefore indicated for use in the treatment of painful inflammation of the joints and periarticular tissue such as occurs in rheumatoid arthritis, Stil's disease, osteoarthritis, various types of non-specific inflammatory or rheumatic conditions affecting the fibro muscular tissue and connective tissue and rheumatic fever and its sequelae. In those cases in which the above conditions include pain, pyrexia, and pruritis, coupled with inflammation, the present compounds are indicated for the relief of these associative conditions as well as the principal condition. The compounds are also useful for the treatment of various dermatoses either by the systemic route or by local application. Specific conditions include contact sensitivity e.g. to chromium, nickel or an antibiotic; eczema; drug eruptions; psoriasis; dermatitis herpetiformis; atopic dermatitis; aphthous ulcers; Behçet's syndrome; pemphigus; urticaria; urticaria pigmentosa; the ulcers of Crohn's disease; pyoderma gangrenosum and chronic skin ulcers, notably those affecting man in tropical climates. The compounds also produce effects, e.g. in mice, which indicates that they have CNS depressant and/or anorectic activity.

For the above mentioned uses the dosage administered will, of course, vary with the compound employed, the mode of administration and the treatment desired. However, in general satisfactory results are obtained when the compounds are administered at a daily dosage of from about 1.0 mg to about 100 mg per kg of animal body weight, preferably given in divided doses 1 to 4 times a day or in sustained release form. For man the total daily dose is in the range of from about 7.0 mg to about 1,400 mg and unit dosage forms suitable for oral administration comprise from about 2.0 mg to about 1,400 mg of the compound admixed with a solid or liquid pharmaceutical carrier or diluent.

The compounds of formula I, and pharmaceutically acceptable salts, esters and amides thereof, may be used on their own or in the form of appropriate medicinal preparations for enteral, parenteral or topical administration. Thus the new compounds may be worked up with inorganic or organic, pharmaceutically acceptable adjuvants, diluents or carriers. Examples of such adjuvants, diluents and carriers are: for tablets and dragées: lactose, starch, talc, stearic acid; for capsules: tartaric acid or lactose; for injectable or topical solutions: water, alcohols, glycerin, vegetable oils; for suppositories or ointments: natural or hardened oils or waxes. We prefer the composition to be in a form suitable for topical or oral administration. We also prefer the composition to contain up to 50% and more preferably up to 25% by weight of the compound of formula I, or of the pharmaceutically acceptable salt, ester or amide thereof.

It is well known that many anti-inflammatory agents currently in use have unwanted gastro-intestinal side effects. The compounds of the present invention have, in general, been found in animal tests to have a lower and/or different pattern of incidence of side effects than some other anti-inflammatory agents. Furthermore the compounds of the present invention appear to exert their effects by a different mechanism to that by which conventional anti-inflammatory agents work.

We prefer that, when they contain carbon, each of R$_3$, and any substituent on ring A or on the R$_1$ phenyl group, contain up to and including 10, and preferably up to and including 7 carbon atoms. We prefer R$_3$ to be chosen from hydrogen; hydroxy; alkyl C 1 to 6; alkyl C 1 to 6 substituted by 1 or 2 carboxy groups; —COOH or a C 1 to 6 alkyl ester or an unsubstituted amide thereof; chloro-phenyl; phenyl; chlorophenylamino; alkoxy C 1 to 6; alkoxy C 1 to 6 substituted by a di- C 1 to 6 alkyl amino group; thioalkoxy C 1 to 6; chlorine; phenoxy; thiophenoxy; cyano; amino; piperidyl; mono- or di- C 1 to 6 alkyl amino the alkyl groups of which may be substituted by C 1 to 6 alkoxy or by a mono- or di- C 1 to 6 alkyl- or by an unsubstituted amino group, N- C 1 to 6 alkyl-piperazino; carboxyureido; —CF$_3$ or acetyl. We prefer R$_1$ to be phenyl substituted by methoxy, methyl, amino, di- C 1 to 6 alkyl amino, methoxycarbonyl, carboxy methyl, chlorine or fluorine. We particularly prefer R$_1$ to be 4-fluorophenyl or 4-chlorophenyl. We prefer R$_3$ to be a substituent other than hydrogen (particularly mono- or di-alkylamino) and the A ring to be unsubstituted or to be substituted by one or more chlorine, —CF₃, acetyl or alkyl C 1 to 10 (preferably C 1 to 6) groups. In ring A the nitrogen when present may be in any of the 5, 6, 7 or 8 positions.

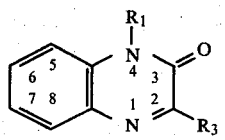

However we prefer the N atom to be in the 5 position.

The invention is illustrated, but in no way limited by the following Examples:

EXAMPLE 1

1-(4-Chlorophenyl)-1,2-dihydro-3-hydroxyquinoxalin-2-one

N-(4-Chlorophenyl)benzene-1,2-diamine (11.2 g) was added to diethyl oxalate (50 ml) and the mixture heated under reflux for 2 hours. The mixture was cooled and ethanol (40 ml) was added. The precipitated solid was filtered off and recrystallised from ethanol giving the title compound (11.2 g) mp>300° C.

Analysis: 61.2%C; 3.4%H; 10.2%N; 12.7%Cl; Required: 61.6%C; 3.3%H; 10.3%N; 13.0%Cl.

EXAMPLE 2

4-(4-Chlorophenyl)-3,4-dihydro-2-hydroxy-3-oxopyrido[2,3-b]pyrazine

Preparation as in Example 1 but using 3-amino-2-(4-chlorobenzeneamino)pyridine gave the title compound mp>300° C.

EXAMPLE 3

1-(4-Chlorophenyl)-1,2-dihydro-3-methylquinoxalin-2-one

Preparation as in Example 1 but using ethyl pyruvate gave the title compound mp 185°-187° C.

Analysis: 66.3%C; 4.4%H; 10.2%N; Required: 66.5%C; 4.1%H; 10.35%N.

EXAMPLE 4

1-(4-Chlorophenyl)-1,2-dihydro-3,6-dimethylquinoxalin-2-one

Preparation as in Example 1 but using N-(4-chlorophenyl)-4-methylbenzene-1,2-diamine and ethyl pyruvate gave the title compound mp 223°-225° C.

Analysis: 67.4%C; 4.8%H; 9.8%N; 12.6%Cl; Required: 67.5%C; 4.6%H; 9.8%N; 12.4%Cl.

EXAMPLE 5

1-(4-Chlorophenyl)-1,2-dihydro-3-ethylquinoxalin-2-one

Preparation as in Example 1 but using ethyl 2-ketobutyrate gave the title compound mp 163°-165° C.

Analysis: 67.6%C; 5.0%H; 9.8%N; Required: 67.5%C; 4.6%H; 9.8%N.

EXAMPLE 6

1-(4-Chlorophenyl)-1,2-dihydro-3,7-dimethylquinoxalin-2-one

Preparation as in Example 1 but using N-(4-chlorophenyl)-5-methylbenzene-1,2-diamine and ethyl pyruvate gave the title compound mp 144°-145° C.

EXAMPLE 7

1,2-Dihydro-3-methyl-1-(4-dimethylaminophenyl)-quinoxalin-2-one

Preparation as in Example 1 but using N-(4-dimethylaminophenyl)benzene-1,2-diamine and ethyl pyruvate gave the title compound mp 230°-231° C.

EXAMPLE 8

1-(4-Aminophenyl)-1,2-dihydro-3-methylquinoxalin-2-one

Preparation as in Example 1 but using N-(4-aminophenyl)benzene-1,2-diamine and ethyl pyruvate gave the title compound mp 269°-271° C.

EXAMPLE 9

1-(4-Carboxymethylphenyl)-1,2-dihydro-3-methyl-quinoxalin-2-one

Preparation as in Example 1 but using N-(4-carboxymethylphenyl)benzene-1,2-diamine and ethyl pyruvate gave the title compound mp 179°-181.5° C.

Analysis: 69.3%C; 5.1%H; 9.5%N; Requires: 69.4%C; 4.8%H; 9.5%N.

EXAMPLE 10

1,2-Dihydro-1-(4-methoxyphenyl)-3-methylquinoxalin-2-one

Preparation as in Example 1 but using N-(4-methoxyphenyl)benzene-1,2-diamine and ethyl pyruvate gave the title compound mp 230°-232° C.

Analysis: 72.2%C; 5.5%H; 10.8%N; Requires: 72.2%C; 5.3%H; 10.5%N.

EXAMPLE 11

1-(3-Trifluoromethylphenyl)-1,2-dihydro-3-methyl-quinoxalin-2-one

Preparation as in Example 1 but using ethyl pyruvate and N-(3-trifluoromethylphenyl)benzene-1,2-diamine gave the title compound.

EXAMPLE 12

4-(4-Chlorophenyl)-3,4-dihydro-2-methyl-3-oxopyrido[2,3-b]pyrazine

Preparation as in Example 1 but using 3-amino-2-(4-chlorobenzeneamino)pyridine and ethyl pyruvate gave the title compound mp 245°-246° C.

Analysis: 61.6%C; 3.7%H; 15.3%N; 12.7%Cl; Requires: 61.9%C; 3.7%H; 15.5%N; 13.0%Cl.

EXAMPLE 13

Ethyl 4-(4-chlorophenyl)-3,4-dihydro-3-oxopyrido[2,3-b]pyrazine-2-carboxylate

Preparation as in Example 1 but using 3-amino-2-(4-chlorobenzeneamino)pyridine and diethyl mesoxalate gave the title compound mp 157.5°-158.5° C.

EXAMPLE 14

3,4-Dihydro-4-(4-methoxyphenyl)-2-methyl-3-oxopyrido[2,3-b]pyrazine

Preparation as in Example 1 but using 3-amino-2-(4-methoxybenzeneamino)pyridine and ethyl pyruvate gave the title compound mp 251°–252° C.

EXAMPLE 15

3,4-Dihydro-2-methyl-4-(4-methylphenyl)-3-oxopyrido[2,3-b]pyrazine

Preparation as in Example 1 but using 3-amino-2-(4-methylbenzeneamino)pyridine and ethyl pyruvate gave the title compound mp 215°–216° C.

Analysis 71.9%C; 5.6%H; 17.0%N; Requires: 71.7%C; 5.2%H; 16.7%N.

EXAMPLE 16

3,4-Dihydro-4-(4-fluorophenyl)-2-methyl-3-oxopyrido[2,3-b]pyrazine

Preparation as in Example 1 but using 3-amino-2-(4-fluorobenzeneamino)pyridine and ethyl pyruvate gave the title compound mp 270°–271° C.

Analysis: 65.6%C; 3.9%H; 16.4%N; Requires: 65.9%C; 3.9%H; 16.5%N.

EXAMPLE 17

1-(4-Chlorophenyl)-1,2-dihydro-3-phenylquinoxalin-2-one

To a solution of N-(4-chlorophenyl)benzene-1,2-diamine (12.0 g) in a minimum quantity of ether was added benzoylformic acid (7.5 g) dissolved in ether and the mixture was stirred for 8 hours. The resulting precipitate was filtered, dried, and recrystallised from ethanol giving the title compound (11.0 g) mp 214.5°–216.5° C.

Analysis: 71.9%C; 4.2%H; 8.3%N; Requires: 72.2%C; 3.9%H; 8.4%N.

EXAMPLE 18

1,2-Dihydro-1-(4-methoxyphenyl)-3-phenylquinoxalin-2-one

Preparation as in Example 17 but using N-(4-methoxyphenyl) benzene-1,2-diamine and gave the title compound mp 199°–202° C.

Analysis: 76.9%C; 5.3%H; 8.3%N; Requires: 76.8%C; 4.9%H; 8.5%N.

EXAMPLE 19

1-(4-Chlorophenyl)-1,2-dihydro-3-methyl-6-trifluoromethyl-quinoxalin-2-one

Preparation as in Example 1 but using ethyl pyruvate and N-(4-chlorophenyl)-4-trifluoromethylbenzene-1,2-diamine.

EXAMPLE 20

3-Chloro-1-(4-chlorophenyl)-1,2-dihydroquinoxalin-2-one

A solution of 1-(4-chlorophenyl)-1,2-dihydro-3-hydroxyquinoxalin-2-one (20 g) in phosphorus oxychloride (64 ml) was refluxed for 4 hours and then poured slowly into iced water. The resulting solid was filtered off, triturated with pentane and dried giving the title compound (19.4 g) mp>300° C.

Analysis: 57.5%C; 2.9%H; 9.5%N; Requires: 57.7%C; 2.7%H; 9.6%N.

EXAMPLE 21

2-Chloro-4-(4-chlorophenyl)-3,4-dihydro-3-oxopyrido[2,3-b]pyrazine

Preparation as in Example 20 but using 4-(4-chlorophenyl)-3,4-dihydro-2-hydroxy-3-oxopyrido[2,3-b]pyrazine and gave the title compound mp>300° C.

EXAMPLE 22

3,4-Dihydro-2-hydroxy-4-(4-methoxyphenyl)-3-oxopyrido[2,3-b]pyrazine

Preparation as in Example 1 but using 3-amino-2-(4-methoxybenzeneamino)pyridine gave the title compound mp>300° C.

EXAMPLE 23

2-Chloro-3,4-dihydro-4-(4-methoxyphenyl)-3-oxopyrido[2,3-b]pyrazine

Preparation as in Example 20 but using 3,4-dihydro-2-hydroxy-4-(4-methoxyphenyl)-3-oxopyrido[2,3-b]pyrazine and gave the title compound mp>300° C.

EXAMPLE 24

3,4-Dihydro-2-hydroxy-4-(4-methylphenyl)-3-oxopyrido[2,3-b]pyrazine

Preparation as in Example 1 but using 3-amino-2-(4-methylbenzeneamino)pyridine gave the title compound mp>300° C.

EXAMPLE 25

2-Chloro-3,4-dihydro-4-(4-methylphenyl)-3-oxopyrido[2,3b]pyrazine

Preparation as in Example 20 but using 3,4-dihydro-2-hydroxy-4-(4-methylphenyl)-3-oxopyrido[2,3-b]pyrazine gave the title compound mp>300° C.

EXAMPLE 26

1-(4-Chlorophenyl)-1,2-dihydro-3-methoxyquinoxalin-2-one

A solution of 3-chloro-1-(4-chlorophenyl)-1,2-dihydroquinoxalin-2-one (7.7 g) and sodium methoxide (2.0 g) in methanol (70 ml) was refluxed for 4 hours. Water was added and the product was extracted into chloroform. Evaporation of the solvent followed by crystallization from ethanol gave the title compound (5.1 g) mp 245°–247° C.

Analysis: 62.9%C; 4.1%H; 10.0%N; 12.1%Cl; Requires: 62.8%C; 3.8%H; 9.8%N; 12.4%Cl.

EXAMPLE 27

4-(4-Chlorophenyl)-3,4-dihydro-2-methoxy-3-oxopyrido[2,3-b]pyrazine

Preparation as in Example 26 but using 2-chloro-4-(4-chlorophenyl)-3,4-dihydro-3-oxopyrido[2,3-b]pyrazine gave the title compound mp 242°–243° C.

Analysis: 58.3%C; 3.7%H; 14.8%N; Requires: 58.4%C; 3.5%H; 14.6%N.

EXAMPLE 28

1-(4-Chlorophenyl)-1,2-dihydro-3-ethoxyquinoxalin-2-one

Preparation as in Example 26 but using sodium ethoxide in ethanol gave the title compound mp 244°–246° C.

Analysis: 63.9%C; 4.6%H; 9.3%N; 12.0%Cl; Requires: 63.9%C; 4.3%H; 9.3%N; 11.8%Cl.

EXAMPLE 29

1-(4-Chlorophenyl)-1,2-dihydro-3-thioethoxyquinoxalin-2-one

Preparation as in Example 26 but using sodium thioethoxide in benzene gave the title compound mp 221°–222° C.

Analysis: 60.9%C; 4.3%H; 8.9%N; 9.7%S; Requires: 60.7%C; 4.1%H; 8.85%N; 10.1%S.

EXAMPLE 30

3-(Bisethoxycarbonyl)methyl-1-(4-chlorophenyl)-1,2-dihydroquinoxalin-2-one

A mixture of diethyl malonate (3.8 g) and sodium (0.55 g) was allowed to react in dry toluene (50 ml) containing dry tetrahydrofuran (40 ml) for 30 minutes. The solution was heated to reflux, and 3-chloro-1-(4-chlorophenyl)-1,2-dihydroquinoxalin-2-one (7.0 g) was added during 3 hours. Water was added and the product was extracted with chloroform. Evaporation of the solvent and crystallisation from cyclohexane gave the title compound (5.4 g) mp 153°–156° C.

Analysis: 61.1%C; 4.9%H; 6.5%N; 8.9%Cl; Requires: 60.8%C; 4.6%H; 6.8%N; 8.6%Cl.

EXAMPLE 31

1-(4-Chlorophenyl)-1,2-dihydro-3-[2-(N,N-diethylamino)ethoxy]quinoxalin-2-one

Preparation as in Example 26 but using sodium 2-(N,N-diethylamino)ethoxide in dry tetrahydrofuran gave the title compound mp 165°–167° C.

Analysis: 65.0%C; 6.3%H; 11.4%N; 9.7%Cl; Requires: 64.6%C; 5.9%H; 11.3%N; 9.6%Cl.

EXAMPLE 32

1-(4-Chlorophenyl)-1,2-dihydro-3-phenoxyquinoxalin-2-one

A mixture of sodium hydride (0.65 g), "15-crown-5" (1,4,7,10,13-pentaoxacyclopentadecane) (0.5 ml), phenol (2.2 g), and dry toluene was stirred for 30 minutes. To this was added a suspension of 3-chloro-1-(4-chlorophenyl)-1,2-dihydroquinoxalin-2-one (6.0 g) in dry toluene (30 ml) and stirring was continued for 2 hours. Water was added and the product was extracted into chloroform. Evaporation of the solvent and crystallisation from ethanol gave the title compound (4.5 g) mp 239°–241° C.

Analysis: 68.6%C; 3.8%H; 7.8%N; 9.95%Cl; Requires: 68.9%C; 3.7%H; 8.0%N; 10.2%Cl.

EXAMPLE 33

1-(4-Chlorophenyl)-1,2-dihydro-3-thiophenoxyquinoxalin-2-one

Preparation as in Example 32 but using thiophenol gave the title compound mp 250°–251° C.

Analysis: 66.0%C; 3.9%H; 7.5%N; 9.8%Cl; 8.7%S; Requires: 65.8%C; 3.6%H; 7.7%N; 9.7%Cl; 8.8%S.

EXAMPLE 34

1-(4-Chlorophenyl)-3-cyano-1,2-dihydroquinoxalin-2-one

A mixture of 3-chloro-1-(4-chlorophenyl)-1,2-dihydroquinoxalin-2-one (10.0 g) and potassium cyanide (2.5 g) in dry dimethylformamide (100 ml) was heated at 140° C. for 24 hours. The mixture was added to water and the product was extracted into chloroform. Evaporation of the solvent and crystallisation of the residue from ethanol gave the title compound (6.3 g) mp 232°–235° C.

Analysis: 63.8%C; 3.2%H; 14.7%N; 12.6%Cl; Requires: 63.9%C; 2.8%H; 14.9%N; 12.6%Cl.

EXAMPLE 35

4-(4-Chlorophenyl)-3,4-dihydro-3-oxo-2-quinoxaline carboxamide 1-(4-Chlorophenyl)-3-cyano-1,2-dihydroquinoxalin-2-one (6.6 g) was heated at 110° C. for 1 hour with polyphosphoric acid (25 g). The mixture was diluted with water and extracted with chloroform. Evaporation of the solvent and recrystallisation of the residue from ethanol gave the title compound (3.8 g) mp 293°–297° (decomp).

Analysis: 60.1%C; 3.4%H; 14.05%N; 12.0%Cl; Requires: 60.1C; 3.3%H; 14.0%N; 11.85%Cl.

EXAMPLE 36

3-Amino-1-(4-chlorophenyl)-1,2-dihydroquinoxalin-2-one

To a melt of ammonium acetate (62 g) at 160° C. was added 1-(4-chlorophenyl)-1,2-dihydro-3-ethoxyquinoxalin-2-one (8.8 g) and the temperature was then raised during 5 minutes to 200° C. and maintained at this level for 15 minutes. The melt was cooled, water was added, and the product was filtered off. Crystallisation from ethanol gave the title compound (5.6 g) mp 254°–255° C.

Analysis: 62.0%C; 3.8%H; 15.3%N; 13.4%Cl; Requires: 61.9%C; 3.7%H; 15.5%N; 13.1%Cl.

EXAMPLE 37

3,4-Dihydro-2-ethoxy-4-(4-methylphenyl)-3-oxopyrido[2,3-b]pyrazine

Preparation as in Example 26 but using 2-chloro-3,4-dihydro-4-(4-methylphenyl)-3-oxopyrido[2,3-b]pyrazine and sodium ethoxide in ethanol gave the title compound which was identified by NMR Delta 1.50 (t) 3H, delta 2.43 (s) 3H, delta 4.59 (q) 2H, delta 7.05–7.45 (m) 5H, delta 7.91 (q) 1H, delta 8.27 (q) 1H.

EXAMPLE 38

2-Amino-3,4-dihydro-4-(4-methylphenyl)-3-oxopyrido[2,3-b]pyrazine

Preparation as in Example 36 but using 3,4-dihydro-2-ethoxy-4-(4-methylphenyl)-3-oxopyrido[2,3-b]pyrazine gave the title compound mp>250° C.

Analysis: 65.5%C; 4.95%H; 21.8%N; Requires: (including 1.82% H$_2$O); 65.5%C; 4.9%H; 21.8%N.

EXAMPLE 39

1-(4-Chlorophenyl)-1,2-dihydro-3-(N-piperidyl)quinoxalin-2-one

A solution of 3-chloro-1-(4-chlorophenyl)-1,2-dihydroquinoxalin-2-one (7.5 g), piperidine (2.4 g), and triethylamine (2.9 g) in ethanol (50 ml) was stirred at 20° C. for 2 hours. Water was added and the product was extracted into chloroform. Evaporation of the solvent and recrystallisation from ethanol gave the title compound mp 184°–185° C.

Analysis: 66.7%C; 5.5%H; 12.0%N; 10.4%Cl; Requires: 67.1%C; 5.3%H; 12.4%N; 10.5%Cl.

EXAMPLE 40

1-(4-Chlorophenyl)-1,2-dihydro-3-ethylaminoquinoxalin-2-one

Preparation as in Example 39 but using ethanolic ethylamine solution gave the title compound mp 192°–195° C.

Analysis: 64.0%; 5.0%H; 14.0%N; 11.75%Cl; Requires: 64.1%C; 4.7%H; 14.0%N; 11.9%Cl.

EXAMPLE 41

1-(4-Chlorophenyl)-1,2-dihydro-3-dimethylaminoquinoxalin-2-one

Preparation as in Example 39 but using ethanolic dimethylamine solution gave the title compound mp 235°–237° C.

Analysis: 63.8%C; 4.8%H; 13.7%N; Requires: 64.1%C; 4.7%H; 14.0%N.

EXAMPLE 42

1-(4-Chlorophenyl)-1,2-dihydro-3-methylaminoquinoxalin-2-one

Preparation as in Example 39 but using ethanolic methylamine solution gave the title compound mp 217°–220° C.

Analysis: 62.6%C; 4.4%H; 14.4%N; 12.8%Cl; Requires: 63.0%C; 4.2%H; 14.7%N; 12.4%Cl.

EXAMPLE 43

1-(4-Chlorophenyl)-1,2-dihydro-3-(N-morpholino)-quinoxalin-2-one

Preparation as in Example 39 but using morpholine in refluxing ethanol gave the title compound mp 203°–205° C.

Analysis: 63.4%C; 4.9%H; 11.9%N; 10.5%Cl; Requires: 63.25%C; 4.7%H; 12.3%N; 10.4%Cl.

EXAMPLE 44

1-(4-Chlorophenyl)-1,2-dihydro-3-(2-methoxyethylamino)quinoxalin-2-one

Preparation as in Example 39 but using 2-methoxyethylamine gave the title compound mp 151°–152° C.

Analysis: 61.7%C; 5.0%H; 12.4%N; 10.7%Cl; Requires: 61.9%C; 4.9%H; 12.75%N; 10.8%Cl.

EXAMPLE 45

3-(4-Chloroanilino)-1-(4-chlorophenyl)-1,2-dihydroquinoxalin-2-one

Preparation as in Example 39 but using 4-chloroaniline and refluxing methanol as solvent gave the title compound mp 258°–260° C.

Analysis: 62.4%C; 3.7%H; 11.2%N; 18.3%Cl; Requires: 62.8%C; 3.4%H; 11.0%N; 18.6%Cl.

EXAMPLE 46

3-(2-Aminoethylamino)-1-(4-chlorophenyl)-1,2-dihydroquinoxalin-2-one

Preparation as in Example 39 but using an excess of diaminoethane in refluxing ethanol gave the title compound mp 173°–174° C.

Analysis: 60.7%C; 4.7%H; 18.1%N; 11.0%Cl; Requires: 61.0%C; 4.8%H; 17.8%N; 11.3%Cl.

EXAMPLE 47

1-(4-Chlorophenyl)-1,2-dihydro-3-(N,N-diethylamino)ethylaminoquinoxalin-2-one

Preparation as in Example 39 but using N,N-diethylethylene diamine in refluxing ethanol gave the title compound mp 96°–98° C.

Analysis: 64.3%C; 6.2%H; 14.7%N; 9.35%Cl; Requires: 64.8%C; 6.2%H; 15.1%N; 9.6%Cl.

EXAMPLE 48

1-(4-Chlorophenyl)-1,2-dihydro-3-(N,N-diethylamino)ethylaminoquinoxalin-2-one dihydrochloride 1-(4-Chlorophenyl)-1,2-dihydro-3-(N,N-diethylamino)ethylaminoquinoxalin-2-one (5.0 g) was dissolved in chloroform (150 ml) and dry hydrogen chloride was bubbled through the solution for 10 minutes. The precipitate was dried and recrystallised from ethanol giving the title compound mp >240° C.

Analysis: 54.4%C; 5.9%H; 12.3%N; 23.6%Cl; Requires: 54.3%C; 5.7%H; 12.7%N; 24.0%Cl.

EXAMPLE 49

1-(4-Chlorophenyl)-1,2-dihydro-3-(4-methylpiperazyl)-quinoxalin-2-one hydrochloride Preparation as in Example 39 but using N-methylpiperazine in refluxing ethanol followed by the method of Example 48 gave the title compound >240° C.

Analysis: 58.0%C; 5.05%H; 14.1%N; 18.35%Cl; Requires: 58.3%C; 5.1%H; 14.3%N; 18.2%Cl.

EXAMPLE 50

1-(4-Chlorophenyl)-3-[3-(N,N-diethylamino)-propylamino]-1,2-dihydroquinoxalin-2-one Preparation as in Example 39 but using 3-diethylaminopropylamine gave the title compound mp 123°–124° C.

The corresponding dihydrochloride was prepared by the method of Example 48 and had mp 202° C. (decomp).

EXAMPLE 51

4-(4-Chlorophenyl)-2-[2-(N,N-diethylamino)ethylamino]-3,4-dihydro-3-oxopyrido[2,3-b]pyrazine Preparation as in Example 39 but using 2-chloro-4-(4-chlorophenyl)-3,4-dihydro-3-oxopyrido[2,3-b]pyrazine and N,N-diethylethylene diamine in refluxing ethanol gave the title compound mp 149°–150° C.

Analysis: 61.3%C; 6.1%H; 19.1%N; 9.7%Cl; Requires: 61.4%C; 5.9%H; 18.8%N; 9.6%Cl.

EXAMPLE 52

2-[2-(N,N-diethylamino)ethylamino]-3,4-dihydro-4-(4-methylphenyl)-3-oxopyrido[2,3-b]pyrazine Preparation as in Example 39 but using 2-chloro-3,4-dihydro-4-(4-methylphenyl)-3-oxopyrido[2,3-b]pyrazine and N,N-diethylethylene diamine in refluxing ethanol gave the title compound mp 131°–132° C.

Analysis: 68.2%C; 7.0%H; 19.9%N; Requires: 68.4%C; 7.1%H; 19.9%N.

EXAMPLE 53

2-[2-(N,N-diethylamino)ethylamino]-3,4-dihydro-4-(4-methoxyphenyl)-3-oxopyrido[2,3-b]pyrazine Preparation as in Example 39 but using 2-chloro-3,4-dihydro-4-(4-methoxyphenyl)-3-oxopyrido[2,3-b]pyrazine and N,N-diethylethylene diamine gave the title compound mp 167°–168° C.

Analysis: 65.1%C; 6.8%H; 19.1%N; Requires: 65.4%C; 6.7%H; 19.1%N.

The corresponding dihydrochloride was prepared by the method of Example 48 and had mp>250° C.

EXAMPLE 54

3,4-Dihydro-4-(4-methoxyphenyl)-3-oxoquinoxaline 2-carboxyureide

To a solution of N-(4-methoxyphenyl)benzene-1,2-diamine (9.0 g) in ethanol (150 ml) was added a solution of alloxan monohydrate (6.7 g) in water (150 ml) and the mixture was stirred for 30 minutes. The precipitate was filtered off and recrystallised from glacial acetic acid giving the title compound mp 236°–238° C.

Analysis: 60.5%C; 4.4%H; 16.8%N; Requires: 60.4%C; 4.1%H; 16.6%N.

EXAMPLE 55

1-(4-Chlorophenyl)1,2-dihydro-3-methyl-6-acetyl-quinoxalin-2-one

Preparation as in Example 1 but using ethyl pyruvate and N-(4-chlorophenyl)-4-acetylbenzene-1,2-diamine.

EXAMPLE 56

1-(4-Chlorophenyl)-1,2-dihydroquinoxalin-2-one (a)
1-(4-Chlorophenyl)-1,2,3,4-tetrahydroquinoxalin-2-one To a stirred solution of 3-chloro-1-(4-chlorophenyl)-1,2-dihydroquinoxalin-2-one (20.0 g) in glacial acetic acid (250 ml) was added zinc powder (20.0 g) in small portions during 30 minutes. After a further 15 minutes the mixture was filtered, water was added and the product was extracted into dichloromethane. Evaporation of the solvent and recrystallisation of the residue from ethanol gave the sub-title compound mp 196°–199° C.

Analysis: 64.6%C; 4.6%H; 10.7%N; 14.0%Cl; Requires: 65.0%C; 4.3%H; 10.8%N; 13.7%Cl.

(b) 1-(4-Chlorophenyl)-1,2-dihydroquinoxalin-2-one

A solution of 1-(4-chlorophenyl)-1,2,3,4-tetrahydroquinoxalin-2-one (8.2 g) in dichloromethane (50 ml) was stirred with manganese dioxide (10.0 g) for 4 hours. The mixture was filtered, evaporated, and the residue was recrystallised from ethanol giving the title compound mp 169°–171° C.

EXAMPLE A

The compounds are tested against the tuberculin reaction in the pleural cavity of guinea pigs using the test described below.

Groups of seven Hartley strain female guinea-pigs in the weight range 250–300 g are sensitized with Freund's complete adjuvant. Each animal receives an intradermal inoculum of 0.05 ml of a 5 mg/ml suspension of finely ground *Mycobacterium tuberculosis* (heat killed, human strains C, DT and PN obtained from the Ministry of Agriculture and Fisheries, Veterinary Laboratories, Weybridge, Surrey, England) in sterile liquid paraffin, into the plantar surface of both hind feet. Four to five weeks later each animal is injected intrapleurally with 5 micro g purified protein derivative in 0.2 ml sterile saline under light halothane anaesthesia.

Two doses of the drug are given orally; the first 1 hour before challenge, and the second 24 hours later. The drugs are administered as finely ground suspensions in arachis oil in a dose volume of 1 ml/kg. The guinea-pigs are killed by $CO_2$ asphyxiation 48 hours after challenge. After dissecting open the thorax the pleural exudate is drawn up into a plastic syringe, the volume measured, and then transferred to a heparinized blood collection tube. When the volume of exudate is less than 1 ml a suitable volume of heparinized saline is added to give a 1 ml sample. The samples are divided for further investigation as follows:

0.5 ml is set aside for total cell count.

0.2 ml is added to 1.8 ml Triton X, a commercially available polyether detergent, in order to lyse the cells, and stored at −20° C. for estimation of total lysosomal enzyme.

The remainder is centrifuged at 2,500 rpm for 10 minutes and a 0.2 ml of the supernatant stored at −20° C. for estimation of free lysosomal enzyme.

Total cell counts are made on a 1 in 500 dilution of the complete exudate using a Coulter counter after contaminating red blood cells have been lysed. Differential cell counts are performed routinely on stained air dired cell smears.

Total and free lysosomal enzyme content (see above) are determined by recording the beta-glucuronidase activity of the original or cell free exudate respectively. Diluted samples are incubated with the substrate, nitrophenol beta-glucuronide, at pH 4.5 for 16 hours. The released nitrophenol was measured at pH 10.4 on a spectrophotometer set at a wavelength of 400 nm. The activity of the enzyme was recorded as optical density units per $10^6$ cells.

Changes in mean exudate volume, mean total cell count, mean total enzyme, and mean free enzyme values were compared with control values using Student's 't' test and the results were regarded as significant when $p<0.05$. Reduction of mean exudate volume and mean free enzyme indicate activity in the drug. Unchanged mean total cell count and mean total enzyme are indicative of lack of toxicity in the drug. It has been found that the compounds of the invention have greater activity than indomethacin in the above test.

We claim:

1. A compound of formula I,

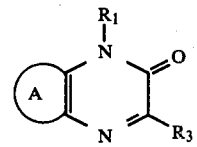

in which $R_1$ is phenyl substituted by halogen, alkoxy, alkyl, carboxy-alkyl, —$NR_4R_5$, carboxy or alkoxy carbonyl, $R_3$ is hydrogen, alkyl, mono- or di-carboxy alkyl, halo, alkoxy, phenyl, halo-phenyl, hydroxy, phenoxy, thiol, thioalkoxy, thiophenoxy, —$NR_4R_5$, cyano, —COOH, carboxyureido, —$CF_3$, —$COR_6$, hydroxyalkyl, aminoalkyl, or alkoxy substituted by $NR_4R_5$, ring A is a pyridine ring which optionally carries up to 4 substituents $R_3$, which may be the same or different, $R_4$ and $R_5$, which may be the same or different, each represent hydrogen, phenyl, halophenyl or alkyl, the alkyl optionally being substituted by alkoxy or by a mono- or di-alkyl or unsubstituted amino group; or $R_4$ and $R_5$, together with the nitrogen atom to which they are attached, form a piperidine, morpholine or an optionally alkyl substituted piperazine ring, and $R_6$ is hydrogen or alkyl, each of $R_3$ and any substituent on ring A or on the $R_1$ phenyl group, when they contain carbon, containing up to and including 10 carbon atoms, provided that when $R_1$ is phenyl substituted by methoxy, $R_3$ is not phenyl, or a pharmaceutically acceptable salt, ester or amide thereof.

2. A compound according to claim 1, wherein each of $R_3$, and any substituent on ring A or on the $R_1$ phenyl group, when they contain carbon, contain up to and including 7 carbon atoms.

3. A compound according to claim 1, wherein $R_3$ is hydrogen; hydroxy; alkyl C 1 to 6; alkyl C 1 to 6 substituted by 1 or 2 carboxy groups; —COOH or a C 1 to 6 alkyl ester or an unsubstituted amide thereof; chlorophenyl; phenyl; chlorophenylamino; alkoxy C 1 to 6; alkoxy C 1 to 6 substituted by a di- C 1 to 6 alkyl amino group; thioalkoxy C 1 to 6; chlorine; phenoxy; thiophenoxy; cyano; amino; piperidyl; mono- or di- C 1 to 6 alkyl amino the alkyl groups of which may be substituted by C 1 to 6 alkoxy or by a mono- or di- C 1 to 6 alkyl- or by an unsubstituted amino group; N- C 1 to 6 alkylpiperazino; carboxyureido; —$CF_3$ or acetyl.

4. A compound according to claim 1, wherein $R_1$ is phenyl substituted by methoxy, methyl, amino, di- C 1 to 6 alkyl amino, methoxycarbonyl, carboxy-methyl, chlorine or fluorine.

5. A compound according to claim 4, wherein $R_1$ is 4-fluorophenyl or 4-chlorophenyl.

6. A compound according to claim 1, wherein $R_3$ is mono- or dialkylamino.

7. A compound according to claim 1, wherein the A ring is unsubstituted or is substituted by one or more —$CF_3$, acetyl, chlorine or alkyl C 1 to 10 groups.

8. A compound according to claim 1 and selected from
4-(4-Chlorophenyl)-3,4-dihydro-2-hydroxy-3-oxopyrido[2,3-b]-pyrazine,
4-(4-Chlorophenyl)-3,4-dihydro-2-methyl-3-oxopyrido[2,3-b]-pyrazine,
Ethyl 4-(4-chlorophenyl)-3,4-dihydro-3-oxopyrido[2,3-b]-pyrazine-2-carboxylate,
3,4-Dihydro-4-(4-methoxyphenyl)-2-methyl-3-oxopyrido[2,3-b]-pyrazine,
3,4-Dihydro-2-methyl-4-(4-methylphenyl)-3-oxopyrido[2,3-b]-pyrazine,
3,4-Dihydro-4-(4-fluorophenyl)-2-methyl-3-oxopyrido[2,3-b]-pyrazine,
2-Chloro-4-(4-chlorophenyl)-3,4-dihydro-3-oxopyrido[2,3-b]-pyrazine,
3,4-Dihydro-2-hydroxy-4-(4-methoxyphenyl)-3-oxopyrido[2,3-b]-pyrazine,
2-Chloro-3,4-dihydro-4-(4-methoxyphenyl)-3-oxopyrido[2,3-b]-pyrazine,
3,4-Dihydro-2-hydroxy-4-(4-methylphenyl)-3-oxopyrido[2,3-b]pyrazine,
2-Chloro-3,4-dihydro-4-(4-methylphenyl)-3-oxopyrido[2,3-b]-pyrazine,
4-(4-Chlorophenyl)-3,4-dihydro-2-methoxy-3-oxopyrido[2,3-b]-pyrazine,
3,4-Dihydro-2-ethoxy-4-(4-methylphenyl)-3-oxopyrido[2,3-b]-pyrazine,
2-Amino-3,4-dihydro-4-(4-methylphenyl)-3-oxopyrido[2,3-b]-pyrazine,
4-(4-Chlorophenyl)-2-[2-(N,N-diethylamino)ethylamino]-3,4-dihydro-3-oxopyrido[2,3-b]pyrazine,
2-[2-(N,N-diethylamino)ethylamino]-3,4-dihydro-4-(4-methylphenyl)-3-oxopyrido[2,3-b]pyrazine,
2-[2-(N,N-diethylamino)ethylamino]-3,4-dihydro-4-(4-methoxyphenyl)-3-oxopyrido[2,3-b]pyrazine.

9. A pharmaceutical composition for treatment of an inflammatory condition comprising an effective amount of a compound according to claim 1, as active ingredient, in admixture with a pharmaceutically acceptable adjuvant, diluent or carrier.

10. A method of treatment of an inflammatory condition which comprises administration of an effective amount of a compound according to claim 1 to a patient suffering from an inflammatory condition.

* * * * *